US00PP35939P2

(12) United States Plant Patent
Flore

(10) Patent No.: US PP35,939 P2
(45) Date of Patent: Jul. 2, 2024

(54) ***PHALAENOPSIS* PLANT NAMED 'MI02415'**

(50) Latin Name: *Phalaenopsis hybrida*
Varietal Denomination: MI02415

(71) Applicant: MICROFLOR N.V., Lochristi (BE)

(72) Inventor: Febe Flore, Lochristi (BE)

(73) Assignee: MICROFLOR N.V., Lochristi (BE)

( * ) Notice: Subject to any disclaimer, the term of this patent is extended or adjusted under 35 U.S.C. 154(b) by 0 days.

(21) Appl. No.: 18/378,051

(22) Filed: Oct. 9, 2023

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — C. Anne Whealy

(57) ABSTRACT

A new and distinct cultivar of *Phalaenopsis* plant named 'MI02415', characterized by its upright plant habit; vigorous growth habit and rapid growth rate; strong flowering stems; relatively compact and arching leaves; freely flowering habit with typically about two to three inflorescences per plant, each inflorescence with numerous flowers; durable deep pink to deep purplish pink-colored flowers with darker reddish purple-colored venation; and excellent postproduction longevity.

2 Drawing Sheets

Figure 1:
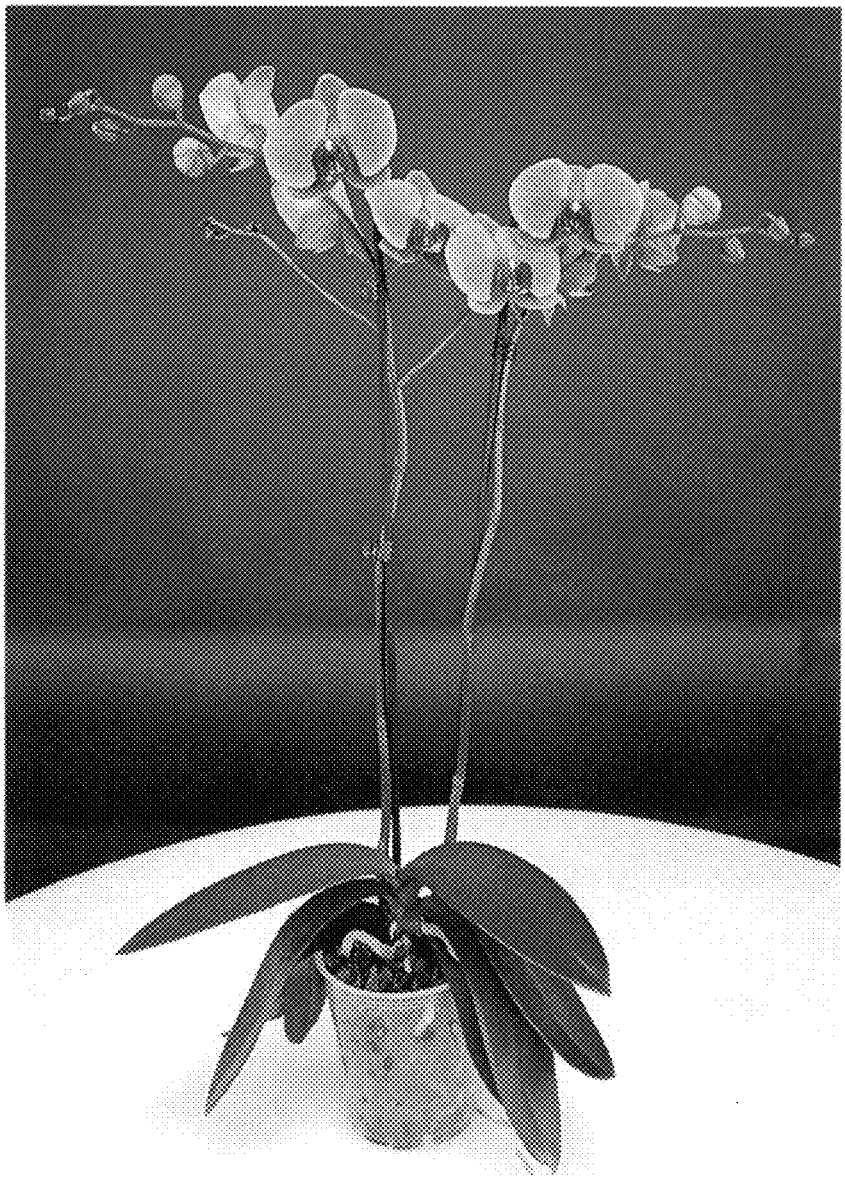

Botanical designation: *Phalaenopsis hybrida.*
Cultivar denomination: 'MI02415'.

CROSS-REFERENCED TO CLOSELY-RELATED APPLICATIONS

An European Community Plant Breeder's Rights application for the instant plant was filed by the Applicant/Assignee of the instant application, Microflor N.V. of Lochristi, Belgium on Aug. 10, 2023, application number 2023/1663. Foreign priority is not claimed to this application.

BACKGROUND OF THE INVENTION

The present invention relates to a new and distinct cultivar of *Phalaenopsis* plant, botanically known as *Phalaenopsis hybrida*, and hereinafter referred to by the name 'MI02415'.

The new *Phalaenopsis* plant is a product of a planned breeding program conducted by the Inventor in Lochristi, Belgium. The objective of the breeding program is to develop new freely flowering *Phalaenopsis* plants with good leaf shape and relatively large flowers with unique and attractive flower coloration.

The new *Phalaenopsis* plant originated from a cross-pollination by the Inventor in March, 2016 in Lochristi, Belgium of a proprietary selection of *Phalaenopsis hybrida* identified as code number PH02309, not patented, as the female, or seed, parent with a proprietary selection of *Phalaenopsis hybrida* identified as code number MI00709, not patented, as the male, or pollen, parent. The new *Phalaenopsis* plant was discovered and selected by the Inventor as a single flowering plant from within the progeny of the stated cross-pollination grown in a controlled greenhouse environment in Lochristi, Belgium in November, 2018.

Asexual reproduction of the new *Phalaenopsis* plant by in vitro meristem propagation in a controlled environment in Lochristi, Belgium since April, 2020 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MI02415'. These characteristics in combination distinguish 'MI02415' as a new and distinct *Phalaenopsis* plant:

1. Upright plant habit.
2. Vigorous growth habit and rapid growth rate.
3. Strong flowering stems.
4. Relatively compact and arching leaves.
5. Freely flowering habit with typically about two to three inflorescences per plant, each inflorescence with numerous flowers.
6. Durable deep pink to deep purplish pink-colored flowers with darker reddish purple-colored venation.
7. Excellent postproduction longevity.

Plants of the new *Phalaenopsis* can be compared to plants of the female parent selection. Plants of the new *Phalaenopsis* differ primarily from plants of the female parent selection in the following characteristics:

1. Plants of the new *Phalaenopsis* are shorter than plants of the female parent selection.
2. Leaves of plants of the new *Phalaenopsis* are shorter than leaves of plants of the female parent selection.
3. Flowers of plants of the new *Phalaenopsis* are deep pink to deep purplish pink in color whereas flowers of plants of the female parent selection are reddish purple in color.

Plants of the new *Phalaenopsis* can be compared to plants of the male parent selection. Plants of the new *Phalaenopsis* differ primarily from plants of the male parent selection in the following characteristics:

1. Plants of the new *Phalaenopsis* are taller than plants of the male parent selection.
2. Leaves of plants of the new *Phalaenopsis* are shorter than leaves of plants of the male parent selection.
3. Flowers of plants of the new *Phalaenopsis* are deep pink to deep purplish pink in color whereas flowers of plants of the male parent selection are pale greenish yellow in color.

Plants of the new *Phalaenopsis* can be compared to plants of *Phalaenopsis hybrida* 'PHALIFQUDI', disclosed in U.S. Plant Pat. No. 26,831. In side-by-side comparisons, plants of the new *Phalaenopsis* differ primarily from plants of 'PHALIFQUDI' in the following characteristics:

1. Leaves of plants of the new *Phalaenopsis* are narrower than leaves of plants of 'PHALIFQUDI'.
2. Flowers of plants of the new *Phalaenopsis* are larger than flowers of plants of 'PHALIFQUDI'.
3. Flowers of plants of the new *Phalaenopsis* last about two weeks longer than flowers of plants of 'PHALIFQUDI'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'MI02415' grown in a container.

Figure 2:
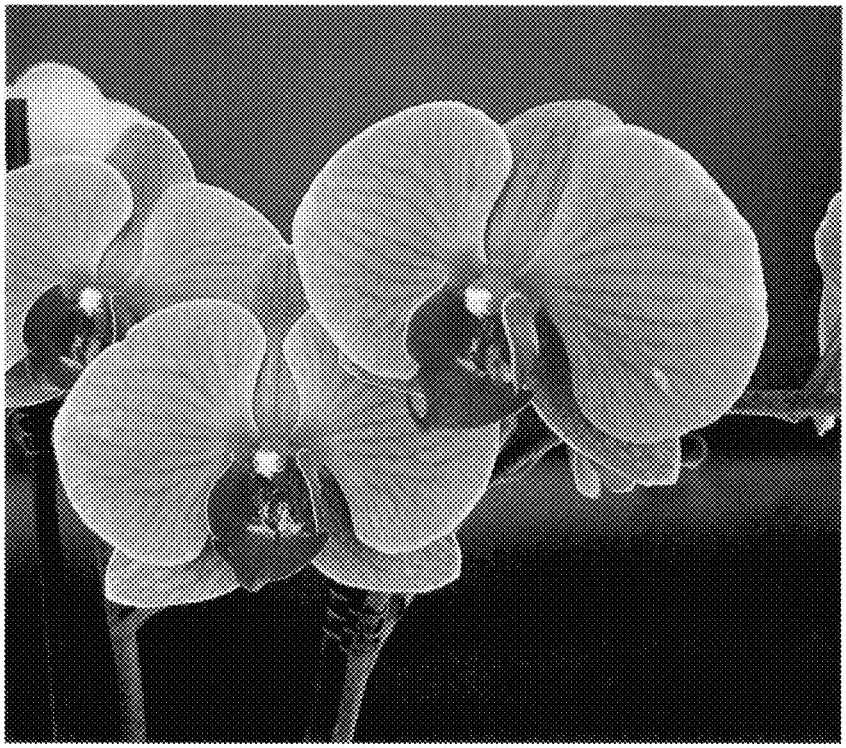

The photograph on the second sheet (FIG. 2) is a close-up view of typical flowers of 'MI02415'.

DETAILED BOTANICAL DESCRIPTION

The aforementioned photographs and following observations and measurements describe plants grown during the summer in 12-cm containers in a glass-covered greenhouse in Lochristi, Belgium and under cultural practices typically used in commercial *Phalaenopsis* production. During the production of the plants, day and night temperatures ranged from 18 C to 29 C and light levels ranged from 150 Watt/$m^2$ to 375 Watt/$m^2$. Plants were 69 weeks old when the photographs were taken and 70 weeks old when the description was taken. In the following description, color references are made to The Royal Horticultural Society Colour Chart, 2001 Edition, except where general terms of ordinary dictionary significance are used.

Botanical classification: *Phalaenopsis hybrida* 'MI02415'.

Parentage:

*Female parent*.—Proprietary selection of *Phalaenopsis hybrida* identified as code number PH02309, not patented.

*Male parent*.—Proprietary selection of *Phalaenopsis hybrida* identified as code number MI00709, not patented.

Propagation:

*Type*.—By in vitro meristem propagation.

*Time to initiate roots, summer*.—About nine to ten weeks at temperatures about 26 C.

*Time to initiate roots, winter*.—About ten to eleven weeks at temperatures about 26 C.

*Time to produce a rooted young plant, summer*.—About 140 to 160 days at temperatures about 26 C.

*Time to produce a rooted young plant, winter*.—About 150 to 180 days at temperatures about 26 C.

*Root description*.—Thick, fleshy; typically grey green in color; actual color of the roots is dependent on substrate composition, water quality, fertilizer, substrate temperature and age of roots.

*Rooting habit*.—Small amount of branching; sparse.

Plant description:

*Plant form and growth habit*.—Herbaceous epiphyte; upright plant habit with typically two to three inflorescences per plant, each inflorescence with numerous flowers; monopodial; vigorous growth habit and rapid growth rate.

*Plant height, substrate level to top of foliar plane*.—About 7 cm.

*Plant height, substrate level to top of inflorescences*.—About 50 cm.

*Plant diameter or spread*.—About 46 cm.

Leaf description:

*Arrangement and quantity*.—Distichous, simple; sessile; about eight leaves per plant; relatively compact.

*Length*.—About 18 cm.

*Width*.—About 7.6 cm.

*Aspect*.—Outwardly arching to somewhat drooping.

*Shape*.—Elliptic to slightly oblanceolate.

*Apex*.—Broadly acuminate; slightly unequal.

*Base*.—Sheathing.

*Margin*.—Entire.

*Texture and luster, upper and lower surfaces*.—Smooth, glabrous; glossy.

*Venation pattern*.—Camptodromous.

*Color*.—When opening, upper surface: Close to 137A; some anthocyanin near edges. When opening, lower surface: Close to 146B tinged with anthocyanin. Fully expanded leaves, upper surface: Close to 137B; venation, close to 137B. Fully expanded leaves, lower surface: Close to 146B slightly tinged with anthocyanin; venation, close to 146B.

Inflorescence description:

*Appearance and flowering habit*.—Showy zygomorphic flowers arranged on axillary branched racemes; typically two to three inflorescences per plant; each inflorescence with about 13 flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about 17 weeks after an inductive cooling period; flowers open about five weeks after flower buds develop.

*Flower longevity*.—Long flowering period and excellent postproduction longevity, individual flowers maintain good substance for about ten weeks on the plant; flowers not persistent.

*Inflorescence length* (*lowermost flower to inflorescence apex*).—About 30 cm.

*Inflorescence width*.—Axially, about 26 cm and radially, about 46 cm.

*Flower buds*.—Height: About 2.3 cm. Diameter: About 2 cm. Shape: Ovate. Color: Close to 161C; venation and towards the edges, close to 53A.

*Flower diameter*.—About 9 cm.

*Flower depth*.—About 4 cm.

*Petals, quantity and arrangement*.—Three, two lateral petals and one center petal transformed into a labellum.

*Lateral petals*.—Length: About 4.2 cm. Width: About 5.5 cm. Shape: Orbicular to deltoid. Apex: Rounded. Margin: Entire. Texture and luster, upper and lower surfaces: Smooth, glabrous, velvety; matte. Color: When opening, upper surface: Close to 51C; venation, close to 70B. When opening, lower surface: Close to 182C. Fully opened, upper surface: Close to 70C; venation, close to 70B; color becoming closer to 186B with subsequent development. Fully opened, lower surface: Close to 73D and towards the margins, slightly darker than 73D; color does not change with subsequent development.

*Labella*.—Appearance: Tri-lobed with two lateral lobes and a central lobe. Length: About 2.8 cm. Width: About 2.4 cm. Shape, lateral lobes: Obovate; apices, obtuse; margins, entire. Shape, central lobe: Deltoid; apices, cleft with narrow recurved cirrose tips; margins, entire. Texture and luster, upper and lower surfaces: Smooth, glabrous, moderately velvety; matte. Callosities: Located at the base of the labellum and attachment point of the lateral petals; about 4 mm in length, about 4 mm in width and about 5 mm in height. Color, lateral lobes, central lobe and callosities: When opening and fully opened, upper surface: Close to 71B. When opening and fully opened, lower surface: Close to 78A.

*Sepals*.—Quantity and arrangement: Three, two lower lateral sepals and one upper dorsal sepal. Length, lateral sepal: About 4.1 cm. Width, lateral sepals: About 2.7 cm. Length, dorsal sepal: About 4.2 cm. Width, dorsal sepal: About 3 cm. Shape, lateral sepals: Oblanceolate; asymmetrical. Shape, dorsal sepal: Elliptical. Apex, lateral sepals: Bluntly acute. Apex, dorsal sepal: Retuse. Base, lateral and dorsal sepals: Rounded. Margin, lateral and dorsal sepals: Entire. Texture and luster, lateral and dorsal sepals, upper and lower surfaces: Smooth, glabrous, velvety; matte. Color, lateral and dorsal sepals: When opening, upper surface: Close to 51C; venation, close to 70B. When opening, lower surface: Close to 165C. Fully opened, upper surface: Close to 70C; venation, close to 70B. Fully opened, lower surface: Close to 186D.

*Peduncles*.—Length: About 65 cm. Diameter, proximally: About 6 mm. Strength: Strong, somewhat flexible. Aspect: Mostly upright. Texture and luster: Smooth, glabrous; matte. Color: Close to 200A; fine lines and dots, close to 148A.

*Pedicels*.—Length: About 4.3 cm. Diameter: About 4 mm. Strength: Moderately strong; flexible. Aspect: About 90 degrees from peduncle axis. Texture and luster: Smooth, glabrous; matte. Color: Close to 74B; mid-section, close to 186B.

*Reproductive organs*.—Androecium: Column length: About 9 mm. Column width: About 5 mm. Column color: Close to 70B. Pollinia quantity: Two. Pollinia diameter (per two pollinia): About 3 mm. Pollinia color: Close to 25A. Gynoecium: Stigma length: About 5 mm. Stigma width: About 3 mm. Stigma shape: Reniform. Stigma color: Close to 76B. Ovary length: About 1.5 mm to 2 mm. Ovary diameter: About 3 mm. Ovary color: Close to 74B. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures of about 40 C and to be suitable for USDA Hardiness Zones 10 and higher.

It is claimed:

1. A new and distinct *Phalaenopsis* plant named 'MI02415' as illustrated and described.

* * * * *